United States Patent [19]
Nacht et al.

[11] Patent Number: 5,840,293
[45] Date of Patent: Nov. 24, 1998

[54] IONIC BEADS FOR CONTROLLED RELEASE AND ADSORPTION

[75] Inventors: Sergio Nacht, Los Altos; Richard Won, Palo Alto; Martin A. Katz, Menlo Park; Tai Cheng; Christine J. Y. Liau, both of Mountain View; Robert P. Eury, Half Moon Bay; Michael Froix, Mountain View, all of Calif.

[73] Assignee: Advanced Polymer Systems, Inc., Redwood City, Calif.

[21] Appl. No.: 245,307

[22] Filed: May 17, 1994

Related U.S. Application Data

[63] Continuation of Ser. No. 8,852, Jan. 25, 1993, abandoned, which is a continuation of Ser. No. 779,681, Oct. 21, 1991, abandoned, which is a continuation-in-part of Ser. No. 272,600, Nov. 16, 1988, abandoned.

[51] Int. Cl.⁶ .............................. A61K 9/14; A61K 7/00
[52] U.S. Cl. ...................... 424/78.02; 424/489; 424/501; 424/401
[58] Field of Search .................... 424/489, 501, 424/401, 78.02, 78.03

[56] References Cited

U.S. PATENT DOCUMENTS

| | | | |
|---|---|---|---|
| 3,691,270 | 9/1972 | Charle et al. | 428/28 |
| 3,761,418 | 9/1973 | Parran | 252/106 |
| 3,880,990 | 4/1975 | Bauer et al. | 424/19 |
| 4,058,491 | 11/1977 | Steckler | 260/2.2 R |
| 4,198,395 | 4/1980 | De Simone | 424/79 |
| 4,221,778 | 9/1980 | Raghunathan | 424/31 |
| 4,256,840 | 3/1981 | Meitzner | 521/33 |
| 4,304,563 | 12/1981 | Grollier et al. | 424/70 |
| 4,351,922 | 9/1982 | Yoshida et al. | 525/116 |
| 4,407,957 | 10/1983 | Lim | 435/178 |
| 4,552,812 | 11/1985 | Margel et al. | 428/407 |
| 4,564,644 | 1/1986 | Harris | 521/28 |
| 4,690,825 | 9/1987 | Won | 424/501 |
| 4,940,588 | 7/1990 | Sparks | 424/489 |

FOREIGN PATENT DOCUMENTS

| | | |
|---|---|---|
| 0060138 | 9/1982 | European Pat. Off. . |
| 0143608 | 6/1985 | European Pat. Off. . |
| 0225615 | 6/1987 | European Pat. Off. . |
| 872554 | 4/1987 | South Africa . |
| 1482663 | 8/1977 | United Kingdom . |

OTHER PUBLICATIONS

Supplier—Interaction Chemicals, Inc., Mountain View, CA (no date available).
Supplier—Reilly Tar & Chemical Corp., Indianapolis, IN (no date available).
Goddard (1987) Cosmetics & Toiletries 102:71–80.

*Primary Examiner*—Sally Gardner-Lane
*Attorney, Agent, or Firm*—Heller Ehrman White & McAuliffe

[57] ABSTRACT

Ionic compositions comprise an active ingredient absorbed within a network of internal pores defined by a plurality of polymeric particles. The particles are preferably crosslinked polymeric beads having a diameter in the range from about 5 to 100 microns and a surface charge density from about 0.1 to 10 meq/qm hydrogen ion capacity. The active ingredients are released from the ionic polymer beads over time when orally administered, applied to a keratinic material, typically human skin or hair or otherwise delivered to a target environment. The use of a cationic charge promotes adhesion of the beads to the keratinic material.

18 Claims, 3 Drawing Sheets

IONIC BEADS FOR CONTROLLED RELEASE AND ADSORPTION

This application is a continuation of application Ser. No. 08/008,852 filed Jan. 25, 1993 (now abandoned), which is a continuation of application Ser. No. 07/779,681 filed Oct. 21, 1991 (now abandoned), which is a continuation-in-part of application Ser. No. 07/272,600, filed Nov. 16, 1988, now abandoned, and the disclosure of which is incorporated herein by reference.

BACKGROUND OF THE INVENTION

1. Field of the Invention

The present invention relates generally to the preparation of topical and oral compositions. More particularly, it relates to the preparation of ionic polymer delivery systems which prolong the activity of various topically active ingredients by increasing the substantivity on keratinic materials, such as hair and skin, and to orally delivered polymers which release active substances via ion-exchange.

The adherent properties of topically-applied substances on hair and skin affects both initial adsorption and retention, particularly on subsequent exposure to water. The combined characteristics of adsorption and retention constitute the property referred to as "substantivity," which can be defined as the ability of a substance to be adsorbed onto keratin and to resist removal by water rinse-off.

An ideal topical substance would have adsorptive affinity for keratinic materials, retain activity for long periods of time, resist being washed away by perspiration and other contact with water, and be free of adverse interactions with other ingredients of which incorporation is desirous. No topical substance has yet been discovered which adequately satisfies all of these objectives.

Some of the most popular topically active preparations available in the market today include, for example, fragrance substances; cosmetic substances, such as lipsticks, make-up and foundation powders; insect repellents; anti-bacterials; acne treatment formulations; hair treatment formulations, such as conditioners and hair growth promoting agents; and skin protection formulations, such as age-prevention agents; and ultraviolet absorbing substances (sunscreens). These ingredients, substances, or formulations may be used alone, or in combination with each other, and may be applied in pure form or diluted in a suitable solvent or carrier.

A frequently observed problem with such topically active substances is the rapid loss of activity after application to the skin. Under usual conditions of heavy perspiration and/or contact with water, concentration of the above substances in their respective topical compositions is either diluted, thereby reducing effectiveness, or washed away, thereby losing all effectiveness. One way to extend activity is by increasing the concentrations of the active ingredient in their respective formulations. However, as concentrations are increased, so too are the risks of toxic and allergic reactions to the user. These reactions often occur with the higher concentrations, even if exposure to the product is relatively short.

A second drawback, unrelated to the safety of administration of such compositions, is the increased expense of using such compositions which are so easily washed away. For instance, to maintain an adequate level of protection from the sun, a sunbather would have to reapply sunscreen each time after entering the water and frequently after perspiring.

It would therefore be highly desirable to provide an approach for increasing the adsorptive affinity of topically active compositions to keratinic materials, and for prolonging the activity of such compositions, while simultaneously reducing the likelihood of toxic and/or allergic reaction to the user.

Compositions and methods for the release of an active substance, such as a drug, from a reservoir over time are known, and numerous specific approaches exist to achieve such controlled release. Two widely practiced approaches are of particular interest to the present invention. In the first such approach, drugs or other active substances are encapsulated or coated with a material which dissolves or degrades in response to a change in environmental conditions. For example, pH-response coatings (referred to as enteric coatings) may be provided on drugs to protect the drug in the low pH environment of the stomach but dissolve when the pH rises as the drug passes to the intestines. Such coatings include cellulose acetate, phthalate-polyvinyl acetate phthalate, hydroxypropylcellulose phthalate, methyl cellulose phthalate, and the like. Although these coatings are very effective in protecting drugs in the stomach, they do not generally provide a controlled release rate once the drug reaches the intestines.

A less widely employed delivery approach utilizes porous polymeric particles for absorbing and releasing drugs and other active substances at a controlled release rate. See, e.g., U.S. Pat. No. 4,692,462, discussed below. In such systems, the diffusion rate of the drug or other active substance through the pores determines the release rate. The diffusion rate, of course, depends on pore size, drug viscosity, temperature, and the like. In the case of drug delivery, drugs absorbed in porous polymeric particles are usually combined in an adhesive or other matrix material as part of a transdermal drug delivery system. In another example, drugs have been adsorbed onto porous resin beads which are then coated with a membrane diffusion barrier, e.g., ethylcellulose, in order to effect sustained release. See, European Patent Application 171 528, discussed below.

One difficulty with these systems is that a coating or blocking agent must be introduced in order to achieve a desired release rate for particular active substances. The physical characteristics of drugs and other active substances may vary widely, including changes in viscosity, charge characteristics, molecular weight, and the like and the release rate in any delivery system may vary widely depending on the nature of the substance which is being delivered. This problem is particularly evident when employing porous particle delivery systems where modification of the pore characteristics can be achieved only within certain limitations. Synthetic resin-based ion exchangers are conventionally produced by post-polymerization modification of preformed, cross-linked beads. For example, anion exchange resins are made from cross-linked polystyrene by halogen-alkylation and subsequent amination. Cation exchange resins can be made by either carboxylation or sulfonylation of the preformed, cross-linked beads. Such ion exchange resins are typically discolored, have capacities for the exchange of ion less than 2 meq/gm, and regeneration can be a lengthy process. Naturally occurring ion exchangers, such as cellulose-based or dextran gels which are made by introducing functional groups onto the cross-linked natural polymers, have gel structures which are not mechanically strong enough to prevent the gel matrix from shrinking or collapsing as the active ingredient is removed. The natural polymer-based materials are unstable in the presence of oxidants or strong acids, at elevated temperatures (e.g., 120° C. for 30 minutes), and because of their biological origins, they will support bacterial and microbial growth.

Thus, it would be desirable to provide improved compositions and methods for the delivery of drugs and other active substances. It would be particularly desirable if the compositions could be readily modified to achieve a desired release rate for active substances having a wide range of physical and chemical characteristics. It would be further desirable if the compositions could be modified to control the release rate of such diverse active substances under a variety of different external conditions, such as pH, temperature, ionic strength, and the like. It would also be desirable if compositions could be readily modified to allow absorption of bile salts in a controlled and predictable manner.

DESCRIPTION OF THE BACKGROUND ART

U.S. Pat. No. 4,690,825, discloses an uncharged polymer bead delivery system suitable for topical application. U.S. Pat. No. 4,304,563 discloses cationic polymers (and methods for their preparation) useful as gels for treatment of keratinic materials, such as hair. European patent application 225615 discloses the use of cationic beads formed from a polystyrene sulfonate-divinyl benzene copolymer for the controlled oral delivery of negatively-charged drugs. South African patent application no. 872554 and U.S. Pat. No. 4,221,778 discloses sulfonic acid cationic ion exchange resin particles which have been impregnated with certain agents to enhance their suitability for oral drug delivery. U.S. Pat. No. 3,691,270 discloses cosmetic compositions for the skin comprising microcapsules formed from an alveolar polymer, including polyvinylpyridine. The microcapsules, however, are uncharged. U.S. Pat. No. 3,880,990 discloses orally-administratable compositions comprising drugs encapsulated in an anionic polymer. U.S. Pat. No. 4,198,395, discloses a charged polymeric resin material which is useful for the treatment of hypercholesterolemia by oral administration. U.S. Pat. No. 4,552,812, discloses the preparation of fluorescent and magnetic anionic beads useful in performing assays. European patent application 060 138 discloses the preparation of porous copolymeric blocks capable of absorbing and acting as a reservoir for liquids, such as perfume. European patent application 143 608 discloses a polymeric bead composition having a releasable lipophilic compound retained therein. British patent 1,482,663 describe polymeric bead compositions capable of holding water-soluble drugs. Cationic polymeric ion exchange resins, including styrene-divinylbenzene copolymers, are commercially available from suppliers such as Interaction Chemicals, Inc., Mountain View, Calif. 94043; and Reilly Tar & Chemical Corp., Indianapolis, Ind. 46204. The ability of cationic materials to adsorb to the skin and hair is discussed in Goddard (1987) Cosmetics & Toiletries 102:71–80.

SUMMARY OF THE INVENTION

The present invention provides for the incorporation of active and inert substances in an ionic polymer bead delivery system to form novel compositions. It has been found that when a cationic functionality is imparted on the surface of the polymeric bead surface, the substantivity of the topically active substances when the beads are applied to the skin or hair is enhanced. Cationic topical polymeric delivery systems according to the present invention are keratinophilic compositions which exhibit an affinity for skin, hair, and other biological molecules and can be used to adsorb bile salts when delivered orally. The anionic delivery systems can deliver basic drugs orally. The ionic polymer bead delivery system comprises crosslinked polymer beads characterized by ionic functionalities on the bead surface, usually positively charged pyridine and quaternary ammonium groups in the cationic beads, and negatively charged sulfonates and carboxylates in the anionic beads. The beads form a porous network capable of retaining large amounts of inert and active substances. The beads are non-collapsible, small diameter, having relatively large pores and a relatively high ratio of pore volume to bead volume.

The cationic polymer bead delivery system having topically active ingredients incorporated therein may be used as a topical product by itself or may be further incorporated into a carrier composition or other cosmetic product. When used alone, the cationic polymeric delivery system with incorporated topically active ingredient is a dry, free-flowing product which can be rubbed directly onto the skin, providing controlled release of the topically active ingredient over a prolonged period of time. In the more usual situation where the cationic polymeric delivery system is incorporated in other carriers, vehicles, solvents, or cosmetic preparations, use of this delivery system avoids incompatibilities, typically chemical or physical interactions, which might otherwise exist between the active ingredient and other ingredients in the topical preparation, or between the active substance and the carrier, vehicle, or solvent.

A variety of physiologically-acceptable solvent or medium may be used as a carrier. To preserve the cationic functionality on the pyridine-based polymeric bead surface in topical formulations, however, the carrier should be at least slightly acidic, preferably being below about 5, and most preferably being in the range from about 3 to 4. With carboxylate-based beads, the carrier should have a pH above about 5. It will often be desirable to incorporate a physiologically-acceptable buffer in the carrier to maintain the pH within the range of interest.

The ionic polymer bead delivery systems may be formed by suspension or inverse suspension polymerization of suitable monomers, at least some of which include functionalities carrying or capable of carrying either a positive or negative charge under the conditions of use, in an immiscible phase (including a porogen for suspension polymerization of non-aqueous monomers). Generally, the monomers (and the porogen if used) are first mixed together and the resulting mixture is then suspended in the immiscible phase. The immiscible phase is then agitated to form droplets of the monomer mixture, and polymerization of the monomer mixture is initiated to form the desired beads.

Cationicity (i.e., cationic functionality) may be obtained using a preformed cationic monomer, e.g., a quaternary amine monomer (which carriers a substantially permanent charge under the conditions of use), or by protonating (or quaternizing) surface functionalities in the formed bead, e.g., protonating a quaternary nitrogen in pyridine with an acid medium. Such protonation may be performed either before or after entrapping the active ingredient, depending on the conditions and the chemical characteristics of the particular ingredient sought to be incorporated.

Anionicity (i.e., anionic functionality) may be obtained by suspending, for example, sulfonated styrenic beads in a basic solution.

In some cases, the topically active substance may be used as a porogen in a one-step process where there will be no substantial degradation of the substance under the conditions of polymerization and the substance is otherwise suitable. More commonly, for more labile ingredients (particularly those which are heat or radiation labile), the compositions of the present invention may be formed using a two-step process. In this process, the polymeric beads may be preformed using a substitute porogen, for example, an alkane, cycloalakane, or aromatic solvent. The beads are formed by suspension polymerization or inverse suspension polymerization and the substitute porogen is extracted from the resulting bead product. The desired active substance may then be introduced into the beads, typically by contact absorption, to create the desired product. Again, the polymeric beads may be rendered cationic or anionic either before or after entrapping the active substance into the delivery system, or by the use of charged monomers. In addition to allowing the incorporation of labile substances, such a two-step preparation process allows greater control over the structure of the bead based on a wider choice of porogen substances in reaction conditions, and thus may be the desired preparatory method even for less labile substances.

In addition to enhanced substantivity, active substances incorporated into the topically applied cationic polymer bead delivery system of the present invention have been found to provide enhanced effectiveness when compared to similar concentrations of the ingredient in non-cationic polymeric bead delivery systems. For example, sunscreen preparations incorporated into systems comprising cationic polymeric beads will be expected to have an enhanced SPF (Sun Protection Factor) rating when compared to otherwise identical preparations comprising a non-cationic polymer bead delivery system.

Orally deliverable polymeric particles according to the present invention comprise ionic polymeric hydrogel particles, each defining a network of internal pores, composed of an ionic monoethylenically unsaturated monomer and a highly water-soluble polyethylenically unsaturated cross-linking monomer. An oppositely charged counter ion is included for rendering the hydrogels neutral. The hydrogels are unique in that the swelling ratio, $r_{sw}$, determined as the ratio of the swollen particle size (water) to the non-swollen particle size (dioxane) is not directly proportional to the amount of cross-linking monomer used during polymerization of the particles, an unexpected result. Further, the equilibrium water fraction (EWF) of the particles upon equilibration with water is directly proportional to the amount of water used during polymerization. These properties allow the ionic hydrogels to function as sustained release ion exchangers whose diffusion path may be adjusted to suit the particular environment and drug delivered. They also allow "blank" hydrogels to adsorb bile salts.

Oral compositions according to the present invention comprise the ionic hydrogels and counterion, wherein the counterion is either inert or pharmaceutically active, such as a drug, and ionically held within the internal pore network. The counter ion is exchanged for a solute ion in a predetermined aqueous environment, such as an animal or human digestive track. In a particular embodiment, the counter ion is a weakly basic, positively-charged drug which is delivered to the gastrointestinal track upon change in pH and/or ionic strength of the gastrointestinal track.

According to the method of making the hydrogel particles of the present invention, the ionic hydrogels are formed by inverse suspension radical polymerization of suitable ionic monomers cross-linked with a monomer that is soluble in aqueous solutions in all proportions. Generally, the ionic monomer is mixed with the counterion and the resulting mixture combined with the water-soluble cross-linking monomer to form an aqueous phase. An initiator is added to the aqueous phase and the resulting mixture suspended in an organic phase. The organic phase is then agitated to form droplets of the aqueous monomer phase, and polymerization of the monomers initiated to form the desired beads from the droplets. The precise dimensions and characteristics of the beads are controlled by varying process parameters such as the amount of water used during polymerization, agitation speed, and varying the amount or type of monomer chosen. Once the ionic hydrogel beads are formed, the beads can either be used as is (if an inert or stable active ingredient was used as counterion) or loaded with an appropriate labile active counterion by repeated exposure to a drug in a chromatographic column, or by prolonged contact of the hydrogel beads with the drug solution.

DETAILED DESCRIPTION OF THE SPECIFIC EMBODIMENTS

Figure 1:
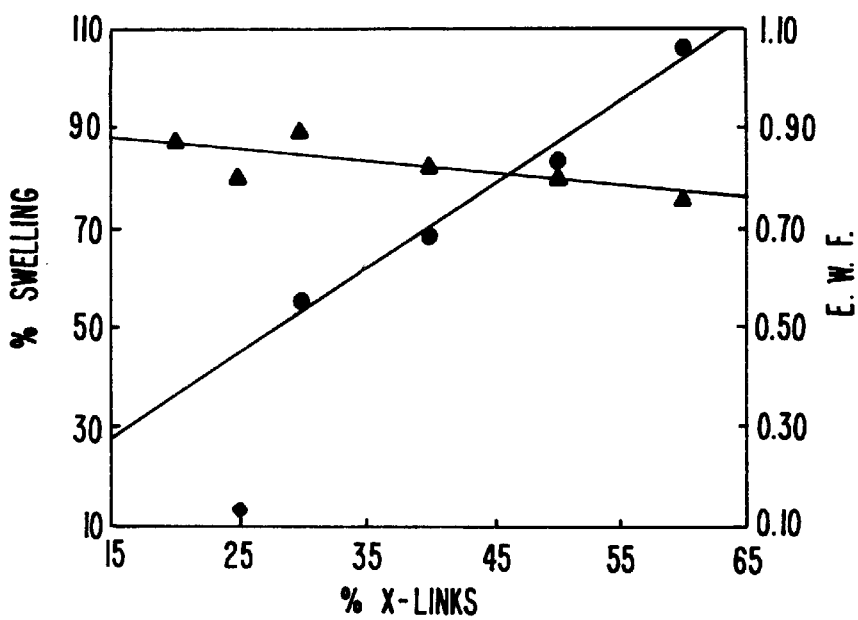
FIG. 1 shows the effect of cross-link density of poly (trimethylammoniumethylmethacrylic chloride-co-N,N'-methylenebisacrylamide) hydrogels on their aqueous swelling ●% swelling v/v; 83% water; ◆% swelling, 70% water; ▲ E.W.F. (equilibrium water fraction), 83% water.

The beads or microspheres used in connection with the present invention can be rigid or non-rigid, and are open-pore, chemical and biologically inert particles, with a positive or negative charge imparted on the surfaces and an impregnant held inside the pores by capillary and ionic forces, where the impregnant is a topically or orally active substance or an inert counter ion. In topical compositions, the charge (positive) is sufficient to promote adhesion of the particles to keratinic materials, such as human skin and hair. The pores are interconnected and open to the particle surface so that substantially full communication is provided between the internal pore space and the exterior of the particle whereby the impregnant may be released over time after the beads are applied to the user's skin or hair, or, in the case of orally delivered drugs, to the GIT.

When cationic beads are used, the cationicity of the polymeric beads of the present invention derives from the presence of a functionality capable of being protonated (or already charged) on at least some of the monomers being polymerized. For oral delivery systems, the beads will have charge density sufficient to produce a binding affinity for a counter ion measured by the weight distribution coefficient method of at least about $1.0 \times 10^6$ ml/gm. (See Lange's Handbook of Chemistry, 13th Edition, pages 5-119–5-122.) The ionic hydrogels will also have porosity and charge density sufficient to afford a counter-ion capacity of at least 45% by weight of total hydrogel. The cationic functionalities of particular interest to the present invention include both pyridine which has a tertiary nitrogen and ammonium which has a quaternary nitrogen, each of which is capable of carrying a positive charge under the conditions of use of the topical compositions. The anionic functionalities of particular interest include sulfonates and carboxylates. Beads according to the present invention will have surface charge densities ranging from about 0.1 to 10 milliequivalent/gram (meq/gm) capacity for hydrogen ion in water (determined by conventional acid-base titration), usually from about 0.2 to 10 meq/gm, more usually from about 0.5 to 10 meq/gm, and preferably from about 5.0 to 10 meq/gm (also determined by conventional acid-base titration).

In their most convenient form, the particles are generally spherical in shape, due to the use of suspension or inverse suspension polymerization as the preferred methods of preparation. While such microspheres vary widely in size, those falling within the range of about 5 to about 100 microns in diameter, preferably from about 10 to about 40 microns, will provide the best results. Microspheres within these size ranges are appealing from an aesthetic point of view by imparting a smooth feel to the touch when applied topically, and are easily expelled when delivered orally.

The pore dimensions within the spheres may also vary widely, with optimum dimensions depending on the chemical characteristics of the polymers used, as well as the diffusive characteristics of the impregnant. Different systems will thus call for different optimum ranges of pore volume distribution to obtain the most desirable properties for the overall formulation. In general, however, the best results are obtained with total pore volumes ranging from about 0.01 to about 4.0 cc/g, preferably from about 0.1 to about 2.00 cc/g, surface areas ranging from about 1 to about 500 $m^2/g$, preferably from about 20 to about 200 $m^2/g$, and the average pore diameters ranging from about 0.001 to about 3.0 micron, preferably from about 0.003 to about 1.0 micron. Following conventional methods of measuring and expressing pore sizes, the pore diameters are calculated from the measurement of the surface area by B.E.T. nitrogen analysis (Brunaer et al. (1938) J. Am. Chem. Soc. 60:309–316) and from the measurement of the pore volumes by the mercury intrusion method.

The particles are conveniently formed as microspheres by suspension polymerization in a liquid-liquid system. In general, a solution containing the desired monomers, a polymerization catalyst (if used), and an inert fluid (porogen) is formed in a first liquid phase, where the porogen is miscible with the first fluid phase but immiscible with a second liquid phase. The solution is then suspended in the second liquid phase which is immiscible with the first liquid phase. In the case of organic-soluble monomers, e.g., vinyl pyridine and its derivatives, the first liquid phase will usually be an organic solvent capable of dissolving the monomers but which is immiscible with water, and the second liquid phase will be water. In the case of water-soluble monomers, e.g., quaternized acrylate and methacrylate derivatives, the first liquid phase will be aqueous (with water as the porogen) while the second phase will be a hydrophobic organic solvent.

Once the suspension is established with discrete droplets of a desired size, polymerization is effected (typically by activating the reactants by either increased temperature or irradiation). After polymerization is complete, the resulting beads are recovered from the suspension. The beads are, at this point, substantially porous structures, the polymer having formed around the inert fluid thereby forming the pore network. The fluid has accordingly served as porogen, or pore-forming agent, and occupies the pores of the formed beads. Suitable porogen fluids will be described in more detail hereinafter. When an organic phase serves as the porogen, the process will be known as suspension polymerization. When water serves as the porogen (in the case of water-soluble monomers), the process will be known as inverse suspension polymerization.

Certain impregnants may serve as porogen and, as previously mentioned, may be entrapped within the porous network of the present invention before or after the charge producing steps described above. The critical factor in choosing the impregnant for topical applications is its electrical charge. That is, in order to preserve the ionic functionality of the beads when applied to the skin or hair, the impregnant must be substantially neutral. Slightly negative or positive substances may be used; however, their entrapment must not neutralize or otherwise affect the surface charge of the bead.

Where the impregnant so selected serves as the porogen, the porous beads recovered from the suspension immediately after polymerization are substantially ready for use, following removal of surface moisture, and any further processing steps of this nature, including ionization. In these cases, microsphere formation and incorporation of the impregnant is performed in a single step. This may accordingly be termed a one-step procedure. Those impregnants which are capable of serving as porogens will be liquid impregnants meeting the following criteria:

1) They are either wholly miscible with a monomer mixture or capable of being made fully miscible by the addition of a minor amount of a solvent which is non-miscible with the second liquid phase;
2) They are immiscible with the second liquid phase (or at most slightly soluble);
3) They are inert with respect to the monomers, and stable when in contact with any polymerization catalyst used and when subjected to any conditions needed to induce polymerization (such as temperature and radiation);
4) They are normally liquids or have melting points below the polymerization temperature. Solids can frequently be converted to liquid form by being dissolved in a solvent or by forming eutectic mixtures; and
5) They are neutral with respect to their electrical charge (or at most either slightly negative or positive).

When using this method, the steps must be performed under an inert atmosphere such as nitrogen. If a polymerization catalyst is used, it must be one which does not oxidize the impregnant, if the latter is susceptible to oxidation. Azo catalysts are examples of such catalysts. Also, polymerization temperatures are being held within a moderate range.

As an alternative to the one-step procedure, the substantially neutral impregnant may be placed inside the pores of preformed dry porous polymer beads. Thus, the product is prepared in two steps, performed in sequence, wherein polymerization is performed first with a substitute porogen which is then removed and replaced by the desired active ingredient. Hence, the porogen and active ingredients are distinct components in this two-step process. Materials suitable as substitute porogens will be substances which meet the five criteria listed above for porogen impregnants.

Preferred among these substances suitable as substitute porogens when hydrophobic monomers are used are hydrocarbons, particularly inert, non-polar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Porogens of other types include $C_4$–$C_{20}$ alcohols, perfluoro polyethers, and oils. Removal of the porogen may be effected by solvent extraction, evaporation, or similar conventional operations. As noted above, in the case of water-soluble monomers, water serves as porogen.

A further advantage of the use of this two-step process is that it permits the removal of unwanted species formed within the polymerized structures prior to incorporation of the impregnant. Examples of unwanted species include unreacted monomers, residual catalysts, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the impregnant as it affects the structure of the bead itself. This permits partial, rather than full, filling of the pores with the impregnant, and further control of the pore size and distribution by selection among swelling and non-swelling porogens.

Extraction of the porogen and its replacement with (i.e., impregnation of the dry bead with) the impregnant in the two-step procedure may be effected in a variety of ways, depending on the chemical nature of the porogen and its behavior in combination with that of the other species present. The beads are first recovered from the suspension by filtration, preferably using vacuum filtration apparatus (such as a Buchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Assuming that the beads were already rendered ionic, or that protonation will follow entrapment (as described in more detail hereinbelow), once the beads are rendered dry and free of the substitute porogen and any unwanted organic materials, they may be used orally as is to absorb oppositely charged species or are impregnated with the impregnant according to conventional techniques. The most convenient such technique is contact absorption. Solid active ingredients are first dissolved in a solvent, and the resulting solution is absorbed by the beads. The solvent may either be retained in the finished product or removed by conventional means such as evaporation or extraction using a further solvent. For those solid ingredients having limited solubility in a particular solvent, high contents in the finished bead can be attained by repeated absorptions each followed by solvent removal.

In the case of oral delivery systems, the impregnant may be, for example, a basic positively-charged drug which is loaded into a matrix of anionic (negatively-charged) beads via chromatographic methods, such as ion exchange chromatography. In that case, the positively-charged counter ion is exchanged with the drug molecules.

The polymerization process and the various parameters and process conditions involved in the polymerization can be selected and adjusted as a means of controlling the pore characteristics and consequently the capacity and release characteristics of the ultimate product. For example, proper selection of the crosslinking means, the amount and type of crosslinking agent, and the amount and type of porogen are means of attaining such control. Certain polymerization conditions may also be varied to such effect, including temperature, degree of radiation where used, degree of agitation and any other factors affecting the rate of the polymerization reaction.

Crosslinking in the polymer formation is a major means of pore size control. Monomers which may be polymerized to produce crosslinked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the percentage of crosslinking may be controlled by balancing the relative amounts of monoethylenically unsaturated monomer and polyethylenically unsaturated monomer. Usually, such systems will include a single monoethylenically saturated monomer and a single polyethylenically unsaturated monomer, although it will be possible to add additional compatible monomers of each type to the system, if desired. For a discussion of the preparation of such copolymer systems, see Guyot and Bartholin, *Design and Properties of Polymers as Materials for Fine Chemistry*, Prog. Polym. Ed. (1982) Vol. 8, pp 303–307.

Monoethylenically unsaturated monomers which may be used as part of the monoethylenically unsaturated monomer content of the polymer delivery system include ethylene, propylene, isobutylene, diisobutylene, styrene, sodium styrene sulfonate, ethylvinylbenzene, vinylbenzene chloride, vinyl pyridine and its derivatives, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; vinyl compounds containing silicon and other metals, such as vinyl siloxanes, and the like. Moreover, polyethylenically unsaturated monomers which ordinarily act as though they have only one unsaturated group, such as isoprene, butadiene and chloroprene, may also be used as part of the monoethylenically unsaturated monomer content.

Polyethylenically unsaturated crosslinking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithioderivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substitute on the benzene nucleus; alkyltrivinylbenzenes having 1 to 3 alkyl groups of 1 to 2 carbon atoms substitute on the benzene nucleus; trivinylnaphthalenes, polyvinylanthracenes, and water-soluble acrylates and methacrylates (as specifically set forth below), and the like.

At least a portion of the monomer content will comprise protonatable functionalities which are capable of retaining a positive charge under the conditions of use. Such protonable functionalities may be present on the monoethylenically unsaturated monomers, the polyethylenically unsaturated monomers, or both, where suitable functionalities include pyridine and ammonium. Exemplary monomers include vinyl pyridines, such as 2-vinyl pyridine, 4-vinyl pyridine, 3-methyl-2-vinyl pyridine, 4-methyl-2-vinyl pyridine, 6-methyl-2-vinyl pyridine, 3-ethyl-2-vinyl pyridine, 5-ethyl-2-vinyl pyridine, 2-methyl-3-vinyl pyridine, 2-methyl-4-vinyl pyridine, 2-methyl-5-vinyl pyridine, and 2-ethyl-5-vinyl pyridine, as well as water-soluble acrylated and methacrylates, such as methacrylamidopropylhydroxyethyldimethylammonium acetate, methacrylamidopropyltrimethylammonium chloride, and the quaternization products of dimethylaminoethylmethacrylate and dimethyl sulfate, diethylaminoethylacrylate and dimethyl sulfate, vinylbenzyl chloride and divinylbenzene, and vinylbenzyl and ethylene glycol dimethacrylate. When quaternized monomers are used, a counter ion such as $Cl^-$, $F^-$, $Br^-$, $I^-$, or $CH_3OSO_3^-$ is incorporated into the structure.

When using the water-soluble acrylate and methacrylate monomers, it is necessary that all monomers employed be water soluble. Suitable polyethylenically unsaturated monomers (required for cross-linking) include N,N'-methylenebisacrylamide; N,N'-nonamethylenebisacrylamide; and alkoxylated water soluble multi-functional acrylates. The inverse suspension polymerization protocol described above for water-soluble quaternized monomers will be employed. The microspheres produced from water soluble quaternized monomers are generally non-rigid hydrogels which are useful for absorbing polar (water and alcohol) soluble materials, such as hydroquinones, methyl salicylate, insect repellents (in alcohols), sunscreens (in alcohol), and the like, while negatively charged hydrogels are useful for absorbing basic drugs, such as alkaloids, steroids, etc.

The preferred polymer bead of the present invention will be free from reactive groups which will react or interact with the porogen and/or the active ingredient which is ultimately incorporated in the composition other than through ionic interaction, such as that seen in ion-exchange processes. Such beads should not readily undergo unwanted reactions, should be stable over the expected pH range of use, should resist moderate oxidation and reduction, will be stable at temperatures within the expected range of use, and should have a relatively long shelf life.

Preferred cationic topical polymer delivery systems of the present invention comprise substantially non-collapsible beads which are formed by the copolymerization of 4-vinylpyridine and ethylene glycol dimethacrylate, 4-vinylpyridine and divinylbenzene, 2-vinylpyridine and divinylbenzene, 2-vinylpyridine and ethylene glycol dimethacrylate, ethyl methyl vinylpyridine and divinylbenzene, and ethyl methyl vinylpyridine and ethylene glycol dimethacrylate. Of these systems, 4-vinylpyridine and divinylbenzene is particularly preferred, while the copolymer of 4-vinylpyridine and ethylene glycol dimethacrylate is even more particularly preferred.

Ionic polymeric hydrogel materials in accordance with the present invention will comprise the copolymerization product of an ionic monoethylenically unsaturated monomer and a polyethylenically unsaturated cross-linking monomer which is soluble in aqueous solutions in all proportions.

Preferred cationic polymers for oral delivery systems are formed from cationic monoethylenically unsaturated quaternary ammonium monomers selected from the group consisting of:

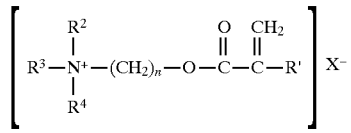

wherein $R^1$, $R^2$, $R^3$, and $R^4$ are the same or different saturated alkyl groups having from one to six carbon atoms, n=1–4, X is selected from the group consisting of Cl, F, Br, I, and $CH_3OSO_3$ and said water-soluble polyethylenically unsaturated cross-linking monomer is selected from the group consisting of N,N'-methylenebisacrylamide, N,N'-nonamethylenebisacrylamide, and alkoxylated water soluble multi-functional acrylates. Particularly preferred cationic polymers include the copolymerization product of trimethylammoniumethylmethacrylic chloride and N,N'-methylenebisacrylamide (poly(PTMAEMCl-co-MBA)).

Preferred anionic polymers for oral delivery systems are formed from the copolymerization product of an anionic monoethylenically unsaturated monomer selected from the group consisting of:

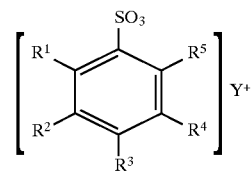

wherein $R^1$, $R^2$, $R^3$, $R^4$, and $R^5$ are the same or different and are selected from the group consisting of H-saturated alkyls having from 1–4 carbon atoms, wherein Y is selected from the group consisting of Na and K, wherein said water-soluble polyethylenically unsaturated cross-linking monomer is selected from the group consisting of N,N'-methylenebisacrylamide, N,N'-nonamethylenebisacrylamide, and alkoxylated water-soluble multi-functional acrylates. Particularly preferred anionic hydrogel beads are the copolymerization products of methacrylic acid and N,N'-methylenebisacrylamide ((poly) MA-co-MBA), and the copolymerization product of sodium styrene sulfonate and N,N'-methylenebisacrylamide (poly(SSS-co-MBA)).

The polymer beads of the present invention will have greater than 10% crosslinking, preferably from about 10% to about 80% crosslinking, and most preferably from about 20% to about 60%. crosslinking. The percentage crosslinking is defined among those skilled in the art as the weight of polyethylenically unsaturated monomer or monomers divided by the total weight of monomer, including both polyethylenically unsaturated and monoethylenically unsaturated monomers. Usually, the monoethylenically unsaturated monomer will be present at from about 20% to 80% of the monomer mixture, preferably 40%, with the polyethylenically unsaturated monomer forming the remainder of the mixture.

In the case of topically applied, neutral impregnants, protonation of the polymeric beads may be performed either before or after entrapping the desired impregnant within the porous network. One way of obtaining the cationic beads of the present invention is, for example, protonating the beads thus recovered from the suspension with an acid medium. In particular, to obtain the positive charge on the surface of the beads of the present invention, an acid wash such as, for example, a 3% aqueous hydrochloride solution, is performed after the beads are recovered from the polymerization step. Excess acid is removed with a second hydrochloride solution having a pH ranging from about 1 to about 4; preferably, however, pH, 3.

Alternatively, the beads of the present invention may be protonated with a pH 3 buffered rinse, comprising 0.1N potassium hydrogen phthalate, 0.1N HCl and deionized water. Use of this buffered rinse does not require removal of excess acid, instead the beads so treated are directly filtered and dried.

Once the microspheres are formed and dried, they may be impregnated with the impregnant by contact absorption (this step may be performed either before or after protonation unless ion-exchange is the method of introducing the active ingredient). As an option, the impregnant may be used in the form of a solution in a suitable organic solvent for purposes of decreasing viscosity and facilitating absorption, decreasing potency, or the like. Examples of such solvents are liquid petrolatum, ether, petroleum ether, alcohols including methanol, ethanol and higher alcohols, aromatics including benzene and toluene, alkanes including pentane, hexane and heptane, ketones including acetone and methyl ethyl ketone, chlorinated hydrocarbons including chloroform, carbon tetrachloride, methylene chloride and ethylene dichloride, acetates including ethyl acetate, and oils including isopropyl myristate, diisopropyl adipate and, mineral oil. After absorption of the solution, the solvent can be evaporated or, if desired, retained inside the pores together with the impregnant. Other formulating materials typically used in topical formulations may be incorporated, such as carriers or adjuvants such as fragrances, preservatives, antioxidants, and other emollients can also be present, and will be incorporated into and onto the beads together with the impregnants and any other materials present.

Substances incorporated in the ionic polymer bead delivery system of the present invention may be used individually or may be combined to achieve a desired effect. The impregnant, whether it be pure active substance, a mixture of active substances or a solution of active substance(s), will generally comprise between approximately 5% and approximately 65% of the total weight of the impregnated beads. When the active substance is particularly potent, it will generally be in the form of a dilute solution, and the weight percent of the active ingredient itself may range as low as 0.01% based on the total weight of the impregnated beads.

Suitable topically active impregnants include a wide variety of active substances intended for topical application, comprising cosmetic, therapeutic, and other uses. Specific substances include ultraviolet absorbing substances (sunscreens), steroids, insect repellents, retinoic acid, fragrances, minoxidil, emollients, and the like. Specific methods for incorporating such substances in polymer bead delivery systems are taught in copending application Ser. Nos. 091,647 and 112,971, the disclosures of which are incorporated herein by reference.

Once the topical compositions have been prepared, by either the one-step or two-step procedures described above, it may be used alone or further incorporated in a carrier or vehicle or in virtually any type of product, provided that they are incapable of neutralizing the surface charge on the bead surface, having at least a slightly acidic pH, preferably being below about pH 6, more preferably having a pH in the range from about 3 to 4. The composition may be used alone by simply applying the composition, which is a dry powder, to the skin.

The impregnated beads useful for topical application of the present invention may also be incorporated in fluid or solid compositions or preparations of the type commonly used for skin treatment, including gels, creams, lotions, ointments, sprays, powders, oils, sticks, and the like. Appropriate vehicles for particular areas or methods of application will be readily apparent to those skilled in the art. For instance, the compositions of the present invention, particularly the UV absorbing compositions, will be incorporated in other products in order to impart cosmetic as well as sunscreen properties. For example, the UV absorbing compositions of the present invention are ideally suited for combining with make-up foundations, suntan preparations, and the like, wherein high adsorption and water-repulsion of the final production is sought.

In the topical composition and formulations of the present invention utilized by application to keratinic material, particularly human skin and hair, the cationic surface charge on the individual polymeric particles promotes adhesion of the compositions to the skin and hair, enhancing the persistence of the active substance which is being applied.

Most often, the ionic hydrogel compositions of the present invention will be used to deliver an active ingredient to a human or other animal for purposes of therapy, hygiene, analgesics, cosmetics, or the like. For such purposes, the compositions may be delivered orally intravascularly, intraoccularly, intraperitoneally, and similar in vivo uses.

The major in vivo use for the hydrogel compositions of the present invention will be for the delivery of drugs and other pharmaceutical agents in human and veterinary applications. Exemplary drugs which may be delivered by the system of the present invention include analgesics, anesthetics, anthelmintics, antimicrobials, antipyrretics, antiseptics, antituburculotics, antitussives, antivirals, cardioactive drugs, cathartics, chemotherapeutic agents, chorticoids (steroids), depressants, diagnostic aids, diuretics, enzymes, expectorants, hormones, hypnotics, minerals, nutritional supplements, parasympathomimetics, potassium supplements, sedatives, sulfonamids, stimulants, sympathomimetics, tranquilizers, urinary anti-infectives, vasoconstrictors, vasodilators, vitamins, xanthine derivatives, and the like.

The anionic hydrogels of the present invention are particularly useful for the oral delivery of cationic drugs which are to be released in the intestines rather than in the stomach. Such drugs include antibiotics, vitamins, non-steroidal anti-inflammatory substances, and the like. The negative surface charge will ionically bind the drug to the hydrogel during storage and while the composition passes through the stomach. On exposure to the high pH environment on the intestines, however, the drug will exchange with positively-charged ions such as sodium and potassium in the intestines in a typical ion exchange process. The drug will then be released from the internal pore network of the hydrogel particles.

In the case of anionic drugs, cationic hydrogels will be used for oral delivery. In that case, bile salts present in the intestines will exchange with the positive surface charge on the beads to effect release of the drugs.

For oral drug delivery, the polymeric hydrogel particles carrying the drug may be incorporated into a variety of known dosage forms, as described in, for example, Remington's Pharmaceutical Sciences, Mack Publishing Co., Easton, Pa., 16th Ed., 1982, the disclosure of which is incorporated herein by reference. The composition or formulation to be administered will contain a preselected quantity of the drug contained within the ionic hydrogel particles. Usually, a pharmaceutically-acceptable non-toxic dosage form is prepared using conventional excipients, such as pharmaceutical grades of mannitol, lactose, starch, magnesium stearate, sodium saccharin, talcum, cellulose, glucose, sucrose, magnesium carbonate, and the like. Such compositions may be in the form of solutions, suspensions, tablets, pills, capsules, powders, and the like.

For parenteral administration, including both intravascular and intramuscular administration, the ionic hydrogel polymeric particles of the present invention will normally be suspended in an injectable water or saline carrier. Such formulations are well known in the art.

The following are some of the considerations specific to various particular types of impregnants, plus examples of preparation and utility. The examples are offered solely for purposes of illustration, and are not intended to limit the invention in any manner. All parts and percentages are by weight, unless otherwise stated.

EXPERIMENTAL

A. Topical Formulations

Example I

This example illustrates the preparation of 4-vinylpyridine/ethyleneglycoldimethacrylate polymeric beads of the present invention. The procedure is set forth below:

A 1000 ml four-necked reaction flask equipped with a motorized stirrer, reflux condenser, thermometer, and nitrogen inlet was evaluated and purged with nitrogen. 300 parts of deionized water, 2.5 parts gum arabic and 2.5 parts lignosulfonate under the trademark Marasperse N-22 (Reed Lignin), were added to the reaction flask. The mixture was heated, with stirring, in an oil bath at about 50° C. until the dispersants (gum arabic and Marasperse N-22) dissolved to form an aqueous phase.

To this mixture was added a solution of 40 parts of 4-vinylpyridine, 60 parts ethyleneglycoldimethacrylate, 0.80 parts benzoyl peroxide (70% active ingredient and 30% water), and 50 parts toluene (porogen). The aqueous phase and organic solution were agitated by stirring at a rate (approx. 900 rpm) adjusted to give a plurality of droplets having a droplet diameter in the range of 5 to 100 microns, as determined by visual observation of a sample of the droplets with an optical microscope with the droplets being stabilized by the dispersants.

The reaction mixture was then heated to 60 to 65° C. for 20 minutes, and heating was continued for another 8 hours at 74°–76° C. to form porous beads of crosslinked 4-vinylpyridine/ethyleneglycoldimethacrylate having toluene entrapped within the network of pores. The reaction mixture was then cooled to room temperature and the porous polymeric beads were removed from the reaction flask by filtration. The filtered beads were washed initially twice with one liter portions of deionized water to remove the dispersants, followed by two washes with one liter portions of isopropanol to remove any residual, unreacted monomers and the toluene. The beads were then dried in an oven at 80° to 90° C. for about 8 hours.

The yield was 87.0 g of opaque beads. The average particle diameter of these beads was 25 microns, as measured by Sedimentation Micromeritics Instrument Co. The particle diameter determination method is described in detail in the *Microsizer* 5300 *Particle Size Analyzer Instruction Manual*, (1984) associated with the instrument.

The surface area of a sample of the purified beads was determined by the B.E.T. Nitrogen Analysis method to be 11.05 $m^2/g$, while the pore volume was determined by the mercury intrusion method to be 0.14 ml/g.

Example II

This example illustrates the protonation of the 4-vinylpyridine/ethyleneglycoldimethacrylate polymeric beads of Example I.

To a 1000 ml flask was added 80.0 g of preformed porous beads from Example I and 300 ml of 3% aqueous hydrochloride solution.

After stirring the slurry for three hours, the porous polymeric cationic beads were filtered and washed with a dilute hydrochloride solution, pH 3, to remove excess 3% acid solution from the polymeric beads. The beads were then dried in an oven at 75° C. for 8 to 10 hours. Hydrogen ion (H+) capacity in water was measured to be 0.78 meq/g.

Example III

This example illustrates the preparation and protonation of 4-vinylpyridine/divinylbenzene polymeric beads. The procedure is set forth below:

The reaction apparatus was prepared as in Example I. To the reaction flask was added 600 parts deionized $H_2O$, 6.0 parts gum arabic, and 6.0 parts Marasperse N-22. The aqueous solution was stirred at room temperature until all solids were dissolved.

To the flask was added an organic solution containing 35 parts 4-vinylpyridine, 65 parts divinylbenzene (55% divinylbenzene, 45% ethylvinylbenzene), 100 parts isobutanol, and 1.0 part 2,2'-azobis (2-methylbutanenitrile) available from the DuPont Co. under the tradename VAZO 67. The reaction mixture was agitated at approximately 1300 rpm until droplets were formed as in Example I. The reaction mixture was then heated to 75° C. at which point agitation was reduced to 800 rpm. The reaction was allowed to continue for 8 hours at this temperature.

Opaque porous beads were collected by filtration and washed three times with 500 ml portions of deionized water. Protonation was effected by stirring the beads in 500 ml of 0.1 N HCl solution for 30 minutes. The beads were filtered and washed with a dilute hydrochloride solution, pH 3, to remove excess acid. Residual monomers and porogen were removed as in Example I. A dry powder was obtained after drying the beads in an 80° to 90° C. oven for approximately 8 hours. The yield was 93 g. The average particle diameter, surface area, and pore volume were 36 micron, 2.21 $m^2/g$, and 0.073 ml/g, respectively.

Example IV

This example illustrates an alternative method for protonizing the polymeric beads of the present invention, using a buffered rinse. The procedure is set forth below:

To a 1000 ml beaker was added 100 g of preformed porous beads from Example I, 250 ml of a pH 3.0 buffer (consisting of 500 parts 0.1N potassium hydrogen 4 phthalate and 223 parts 0.1N HCl), and 250 ml deionized $H_2O$. This mixture was stirred for 30 minutes, then filtered. The quaternized beads were dried in an 80° to 90° C. oven for 6 to 10 hours.

Example V

This example illustrates the preparation of 4-vinylpyridine/ethyleneglycoldimethacrylate beads using xylene as the porogen. The procedure is set forth below:

A 1000 ml reaction flask was charged with an aqueous dispersion solution as described in Example I. An organic solution was prepared as in Example I, with the exception of using 50 parts xylenes (a mixture of ortho, meta and para isomers) as porogen rather than toluene. The reaction was agitated at 1300 rpm until droplet sizes ranged from 10 to 60 microns. The reaction was then heated to 65° C. and maintained at this temperature for 20 minutes. Agitation was reduced to 800 rpm, and the reaction was heated to 75° C. The reaction was allowed to continue at this temperature for 8 hours.

The porous beads were collected by filtration and rinsed with 500 ml deionized $H_2O$. The beads were then quaternized with a pH 3.0 buffer as described in Example IV. The residual monomers and porogen were removed by rinsing the beads three times with 500 ml portions of acetone. After drying approximately 8 hours in a 80° to 90° C. oven, 61g of beads were obtained. The average particle diameter, surface area, and pore volume were 22.5 microns, 3.03 $m^2$/g, and 0.68 ml/g, respectively.

Example VI

This example illustrates the substitution of an ultraviolet absorbing substance (sunscreen) in the cationic beads of Example II. The procedure is set forth below:

An 18.0 parts portion of the porous cationic polymeric beads obtained from Example II was mixed at room temperature with 30 parts of isopropanol in a glass flask with an agitator. Then 12.0 parts of a sunscreen mixture containing 7 parts octyldimethyl PABA and 2 parts Oxybenzone were added slowly. The resulting suspension was stirred for about 20 minutes. The solvent was then allowed to evaporate to dryness in a fume hood at room temperature for 24 hours. Approximately 40% of the sunscreen mixture was entrapped within the pores of the cationic polymeric beads.

Example VII

The adherence and retention of the 4-vinylpyridine/ethyleneglycoldimethacrylate (4-VP/EGDMA) copolymer beads to human skin was investigated in two human subjects. Unprotonated and protonated 4-VP/EGDMA beads were prepared as described in Examples I and II, above, and loaded with an oil soluble dye (Oil Red EGN). The dye was extracted from a small sample of beads and the percentage loading (wt. dye/ (wt. dye+beads)×100) was quantitated using a spectrophotometric method. The unprotonated beads were found to have 0.9% loading while the protonated beads were found to have 1.0% loading.

Measured amounts of each bead preparation (one polymer on each hand) were applied to the marked areas of the forearms of the subjects covering an area of 6.14 $cm^2$. The arms were then immersed in water for five seconds and then removed. This cycle was repeated five times (the hands were not dried between dips), and the polymer retained on the skin was recovered by washing with surfactant solution. The amount of beads retained was determined by extracting out the dye, quantitating it using a spectrophotometric method and correlating the amount of dye extracted to the amount of polymer. The results are present in Table 1.

TABLE 1

| Polymer Beads | Subject | Amount Applied/ $cm^2$ (mg) | Amount Retained (mg)/$cm^2$ | % Retained |
|---|---|---|---|---|
| Unprotonated | 1 | 1.86 | 0.67 | |
| | 2 | 1.89 | 0.61 | 34.26 |
| Protonated | 1 | 1.61 | 0.81 | |
| | 2 | 1.86 | 1.25 | 58.93 |

The results demonstrate that a greater amount of the protonated polymer was retained on the skin compared to the unprotonated polymer.

B. Ionic Hydrogels:

Preparation and Oral Formulations

Example VIII

This example illustrates the preparation of PTMAEMCL cationic hydrogel beads using inverse suspension polymerization.

The following materials are used:

Continuous Phase

The continuous phase is premixed with the following components:

| EMSORB 2500 (Sorbitan monooleate) | 24 g |
|---|---|
| Heptane | 600 g |

The EMSORB 2500 was easily mixed with heptane by hand stirring.

Discontinuous Phase

The discontinuous phase is premixed with the following components:

| Deionized Water | 300 ml |
|---|---|
| Potassium persulfate | 1.8 g |
| MBA | 30 g |
| Sipomer (TMAEMCL) | 90 g |

The MBA was dissolved in water at a temperature of about 55°–60° C. The sipomer was then mixed with the solution when the MBA was completely dissolved. An initiator ($K_2S_2O_8$) was then added. The discontinuous phase solution was kept at a temperature below 64° C. before mixing with the continuous phase.

The continuous solution was preheated in a 2 liter reaction kettle at 60° C. The reaction kettle was purged with nitrogen for about one-half hour before the addition of the monomers. Agitation was begun at 1000 rpm and the monomer solution added to the reaction kettle. The reaction temperature was increased to 75° C. Polymerization started gradually at about 64° C., with no significant exothermal foaming observed during polymerization.

The agitation speed was reduced to 600 rpm after formation of the hydrogel beads, and the stirring rate was kept at 600 rpm for 6 hours at 75° C.

After the reaction vessel had cooled, the mixture was filtered and washed with deionized water until the filtrate was colorless.

The hydrogel beads were then suspended in 500 ml methanol and stirred for one-half hour and again filtered.

This process was repeated twice until the filtrate was colorless. The hydrogel beads were again washed with water to make sure there was no residual monomer left in the filtrate (if the filtrate was hazy, the washing steps were repeated until the filtrate became clean). Once the filtrate was colorless, the hydrogel beads were washed with a mixture of a solution of methanol and acetone (1:1) and the hydrogel beads gradually dried by increasing the ratio of acetone. The hydrogel beads were set still in the evacuation hood for evaporating out the acetone. The hydrogel beads were then dried in a vacuum oven at 50° C. for 8 hours. Photomicrographs of the beads were taken both before and after swelling. These are shown in FIG. 1.

Characterization of Hydrogel Beads

Figure 2:
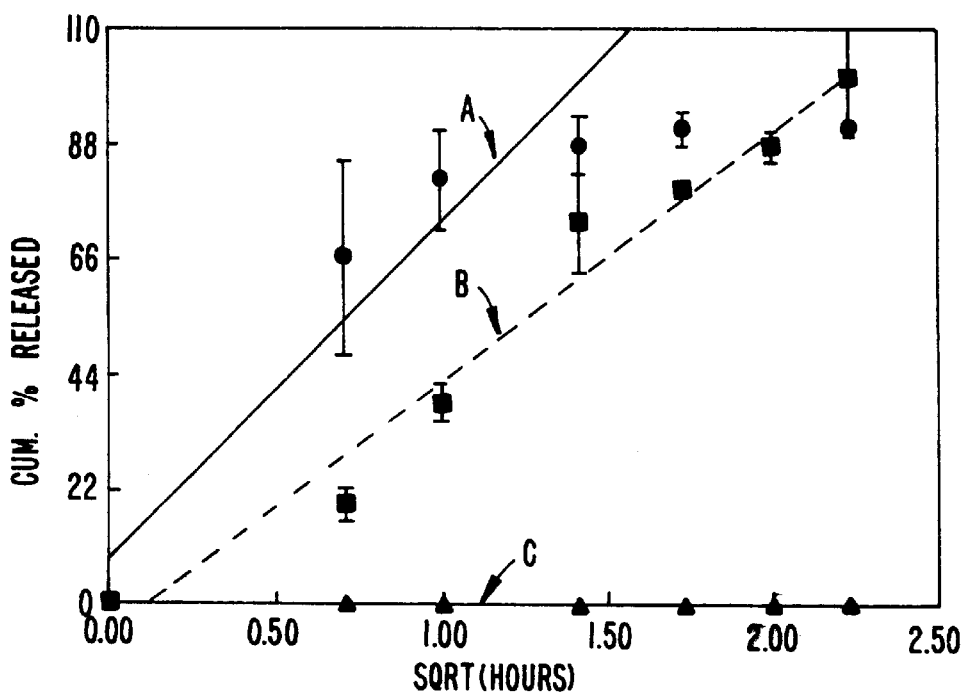
FIG. 2 shows release profiles of D&C Red No. 28 from various beads, including a cationic hydrogel (■); a cationic hydrogel in an anionic surfactant (▲); and an uncharged bead (●).

Cationic hydrogels made as in Example VIII were made with 20%–60% cross-linked content according to the procedure described above. The gels were cast into square discs (2.5 cm.×2.5 cm.×0.16 cm.) in order to investigate the amount of water that the microgels could absorb. The equilibrium water fractions (EWF) were measured as the weight change between the swollen and dried discs. The EWF decreased from 0.85 to 0.78 as the cross-linked content increased from 20% to 80% (FIG. 1). The discontinuous phase for all the samples contained 83% water by weight. The release profile of D&C Red No. 28 was indicative of a controlled release trigger (FIG. 2). FIG. 2 shows a comparison of a macroporous bead alone (curve A), a cationic hydrogel in accordance with the present invention (curve B) when mixed with an anionic surfactant (to simulate biosalts), and a cationic hydrogel (curve C) in a neutral surfactant (polyox) no detectable release occurred when the ionic hydrogels were incubated in either water or water plus non-ionic surfactant (0.5% polyox). However, the dye was released when the sample was added to a release fluid containing anionic surfactant (0.5% sodium lauryl sulfate). The release rate was slower than the control (curve A) and was the result of an ion exchange mechanism wherein the anionic surfactant (simulating biosalts) with exchange for the anionic dye which was complexed to the cationic polymer.

Figure 3:
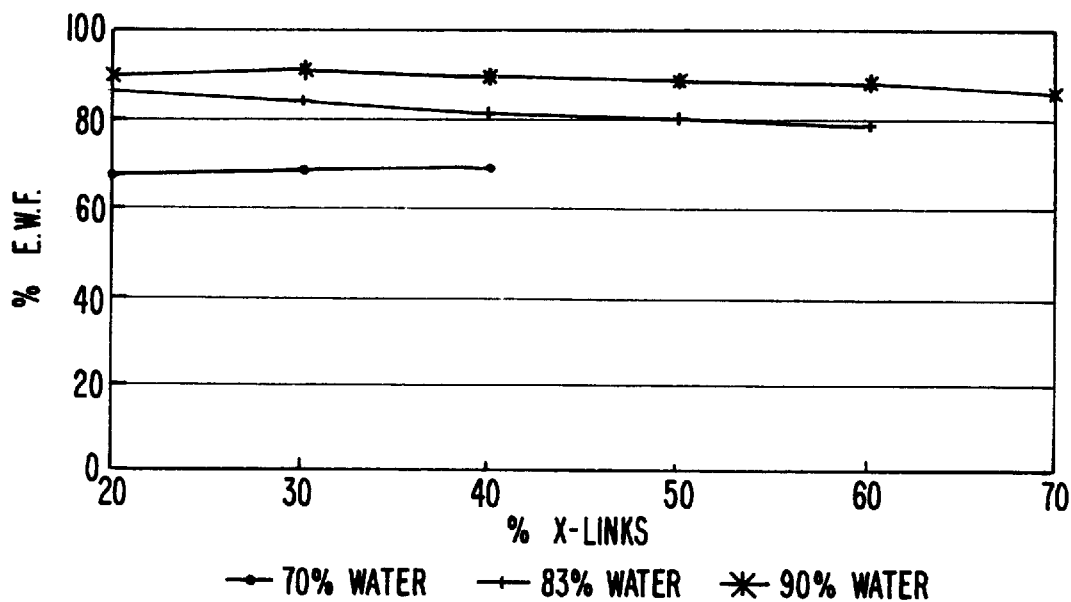
FIG. 3 shows how the equilibrium water fraction of the hydrogels increases in direct proportion to the water content during polymerization and is substantially independent of the cross-linked density.

The relationship between equilibrium water fraction as a function of the water content during polymerization and cross-linked density was determined by measuring the weight gain of hydrogel discs which were swollen in water. FIG. 3 shows how the equilibrium water fraction of the hydrogels increases in direct proportion to the water content during polymerization and is substantially independent of the cross-linked density. This indicated that the hydrogels were polymerized in a greatly distended form which then became the limiting factor for subsequent hydration. The ionic hydrogel was poly(TMAEMCl-co-MBA).

Figure 4:
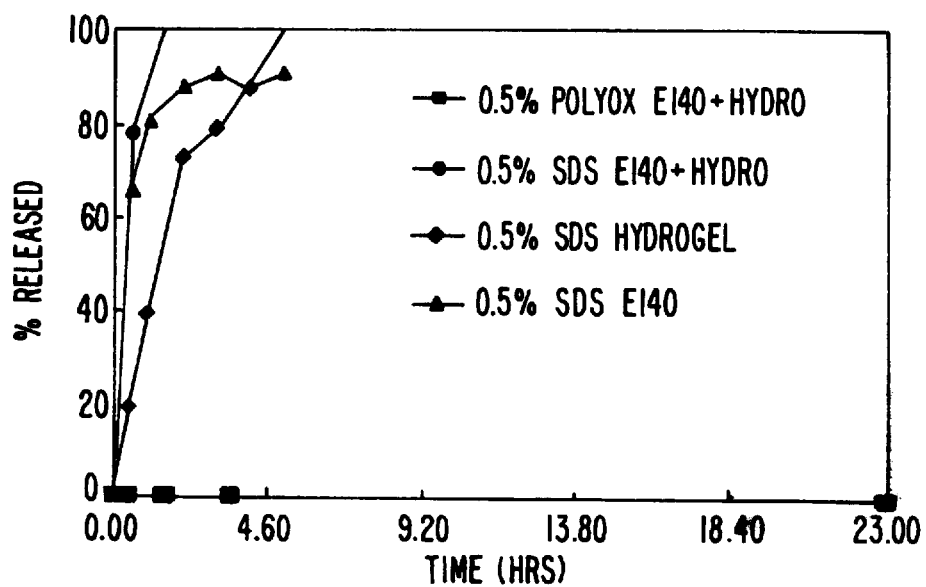
FIG. 4 shows that no D&C Red No. 28 (an anionic dye) was released from a cationic hydrogel loaded macroporous carrier until an anionic surfactant (sodium dodecyl sulfate) was present.

The same general type of material was polymerized inside the pores of a macroporous material, such as that produced and disclosed in U.S. Pat. No. 4,690,825. Representative release profiles of D&C Red No. 28 are shown in FIG. 4 for release fluids which contain either Polyox or SDS surfactant. As was shown for the hydrogel systems, no anionic dye was released from the cationic gel-loaded sponges until an anionic surfactant (SDS) was present. The release rate of dye into the SDS release fluid was the same as the microsponge material with no gel. Thus, several mechanisms are available for manipulating the release profiles of active ingredients via ionic hydrogel loaded microsponges. The hydrogel could swell when exposed to water and thus release active ingredients by squeezing the active out of the pores or the hydrogel could act as a dense coating or plug which does not become permeable to active until swollen. Further, the hydrogels could control the release of ionic actives through ion exchange mechanisms as already demonstrated.

Example IX

The poly(TMAEMCl-co-MBA) hydrogels discussed in Example VIII contain stable cationic charges (quaternary amine groups) which were shown to entrap acidic types of ingredients and not release those ingredients until exposed to an anion suitable for exchange. Many pharmaceutically active substances are basic materials, thus the previous basic hydrogel materials do not bind the basic drugs. Therefore, poly(methacrylic acid-CO-N, N'-methylenebisacrylamide), [poly(MA-CO-MBA)] hydrogels were synthesized to broaden the applicability of the hydrogels to basic active ingredients, for example, alkaloids.

Hydrogels consisting of 10%–15% cross-linking (W/W) were prepared by the inverse suspension polymerization as discussed in Example VIII. As was seen for the poly (TMAEMCl-co-MBA) hydrogels, poly(MA-co-MBA) materials with a lower cross-linked content tended to clump during drying.

Figure 5:
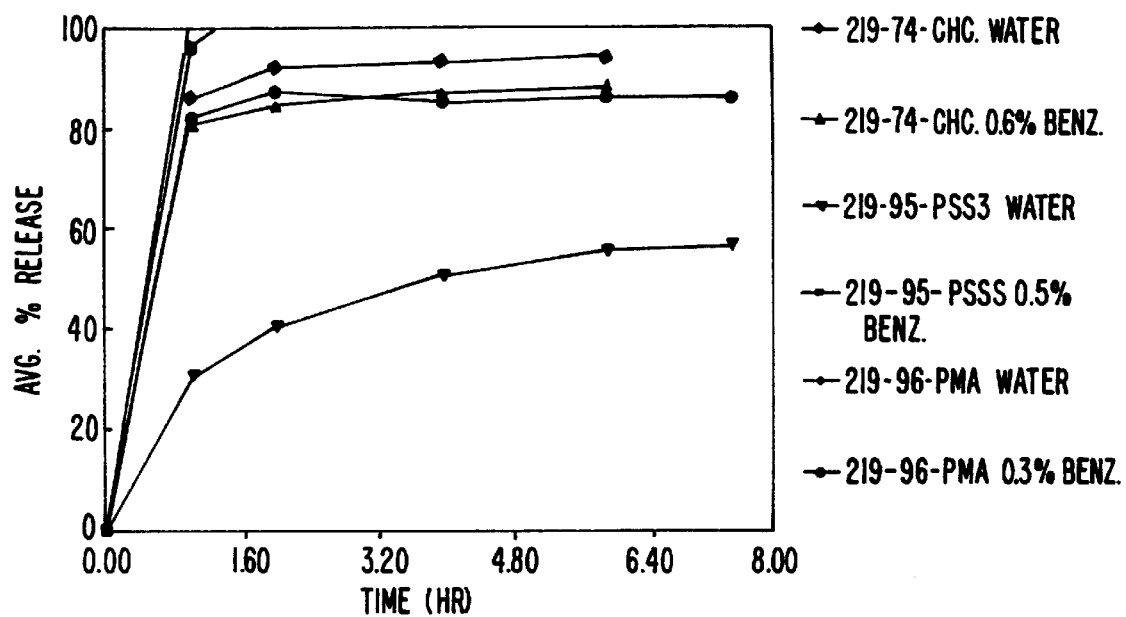
FIG. 5 shows release profiles of tetracycline-HCl from anionic hydrogels when a cationic surfactant is added.

Tetracycline-HCl was chosen as the model basic active ingredient for the release rate studies since it was UV detectable and water soluble. The release characteristics of tetracycline-HCl into deionized water from swollen gel matrices was determined for 50% cross-linked beads. The effect of the gels charge density on the tetracycline-HCl diffusion coefficient was also investigated for release fluids containing 0.5% benzalkonium chloride, a cationic surfactant. The release profile (FIG. 5) of tetracycline-HCl from poly(MA-co-MBA) polymer systems into dissolution mediums of 0.5% benzalkonium chloride or water did not show much difference from that of the control.

Figure 6:
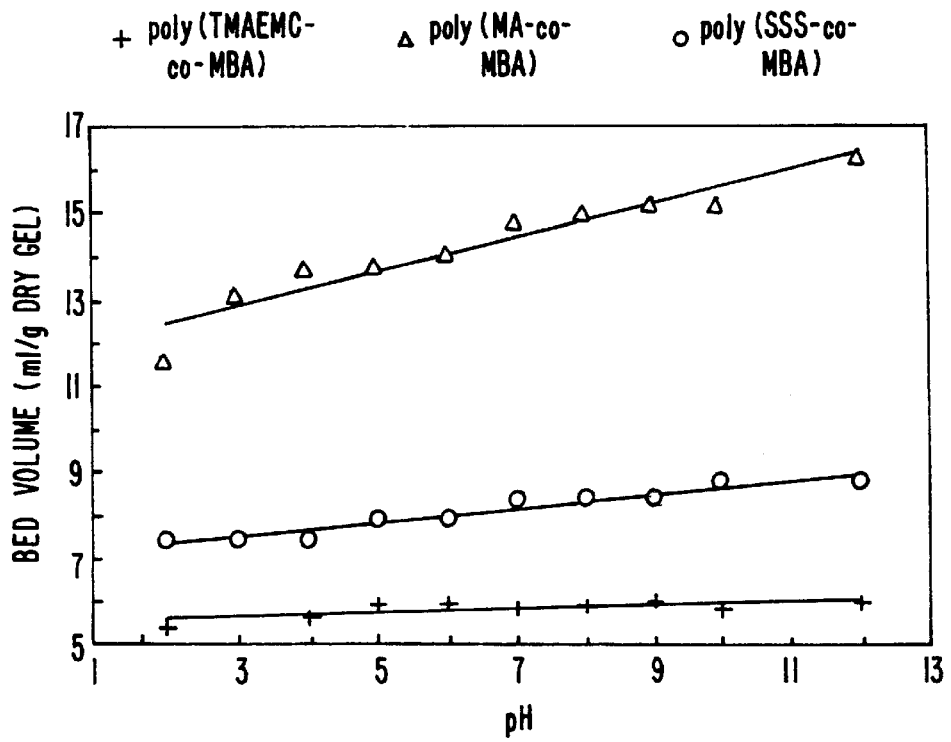
FIG. 6 shows the swelling behavior of hydrogels as a function of pH.

FIG. 6 shows the swelling behavior of cationic and anionic hydrogels as a function of pH. The charge density on poly(TMAEMCl-co-MBA), 25% TMAEMCL, and poly (SSS-co-MBA), 30% SSS, are independent of pH. Therefore, the swelling behavior of these materials was independent of pH. The charge density on poly(MA-Co-MBA), 10% MA, is a function of pH with the material becoming more negatively charged at higher pH. Thus, the degree of swelling increases with increasing pH for this material. The swelling was determined by placing one gram of dry material into a graduated cylinder and adding the buffer solution to a depth of 25 cm. The material and buffer were allowed to equilibrate before the volume reading was taken.

Although the foregoing invention has been described in some detail by way of illustration and example for purposes of clarity of understanding, it will be obvious that certain changes and modifications may be practiced within the scope of the appended claims.

What is claimed is:

1. A topical composition comprising:
   (a) a carrier suitable for topical application having a pH below about 6;
   (b) substantially non-collapsible polymeric beads, each bead having an exterior surface and defining a network of internal pores open to the exterior surface, the exterior surface of each bead having a positive charge sufficient to promote adhesion of the bead to keratinic materials, dispersed within the carrier, the beads being formed from a crosslinked polymer bearing protonatable functionalities that are capable of retaining a cationic charge, the crosslinked polymer comprising a vinylpyridine selected from 2-vinylpyridine, 4-vinylpyridine, 3-methyl-2-vinylpyridine, 4-methyl-2-vinylpyridine, 6-methyl-2-vinylpyridine, 3-ethyl-2-vinylpyridine, 5-ethyl-2-vinylpyridine, 2-methyl-3-vinylpyridine, 2-methyl-4-vinylpyridine, 2-methyl-5-vinylpyridine, and 2-ethyl-5-vinylpyridine; and (c) a substantially neutral impregnant that is a therapeutically or topically active substance retained inside the pore network of each bead.

2. The composition of claim 1 where the beads are substantially spherical in shape and have an average diameter of about 1 micron to about 125 microns, a total pore volume of about 0.01 cc/g to about 4.0 cc/g, an average surface area of about 1 $m^2/g$ to about 500 $m^2/g$, an average pore diameter of about 0.001 micron to about 3.0 micron, and a crosslinking density of at least about 10%.

3. The composition of claim 2 where the surface charge on the beads is from about 0.1 to about 10 meq/g hydrogen ion capacity.

4. The composition of claim 1 where the vinylpyridine is 4-vinylpyridine.

5. The composition of claim 4 where the crosslinked polymer is a copolymer of 4-vinylpyridine and ethylene glycol dimethacrylate.

6. The composition of claim 4 where the crosslinked polymer is a copolymer of 4-vinylpyridine and divinylbenzene.

7. The composition of claim 1 where the impregnant is selected from ultraviolet absorbing substances, steroids, insect repellants, retinoids, fragrances, minoxidil, and emollients.

8. The composition of claim 7 where the impregnant is an ultraviolet absorbing substance.

9. A method for topically applying a therapeutically or topically active substance to a keratinic material, the method comprising applying to the keratinic material a topical composition comprising:

(a) a carrier suitable for topical application having a pH below about 6;

(b) substantially non-collapsible polymeric beads, each bead having an exterior surface and defining a network of internal pores open to the exterior surface, the exterior surface of each bead having a positive charge sufficient to promote adhesion of the bead to keratinic materials, dispersed within the carrier, the beads being formed from a crosslinked polymer bearing protonatable functionalities that are capable of retaining a cationic charge, the crosslinked polymer comprising a vinylpyridine selected from 2-vinylpyridine, 4-vinylpyridine, 3-methyl-2-vinylpyridine, 4-methyl-2-vinylpyridine, 6-methyl-2-vinylpyridine, 3-ethyl-2-vinylpyridine, 5-ethyl-2-vinylpyridine, 2-methyl-3-vinylpyridine, 2-methyl-4-vinylpyridine, 2-methyl-5-vinylpyridine, and 2-ethyl-5-vinylpyridine; and (c) a substantially neutral impregnant comprising the therapeutically or topically active substance retained inside the pore network of each bead.

10. The method of claim 9 where the beads are substantially spherical in shape and have an average diameter of about 1 micron to about 125 microns, a total pore volume of about 0.01 cc/g to about 4.0 cc/g, an average surface area of about 1 $m^2/g$ to about 500 $m^2/g$, an average pore diameter of about 0.001 micron to about 3.0 micron, and a crosslinking density of at least about 10%.

11. The method of claim 10 where the surface charge on the beads is from about 0.1 to about 10 meq/g hydrogen ion capacity.

12. The method of claim 9 where the vinylpyridine is 4-vinylpyridine.

13. The method of claim 12 where the crosslinked polymer is a copolymer of 4-vinylpyridine and ethylene glycol dimethacrylate.

14. The method of claim 12 where the crosslinked polymer is a copolymer of 4-vinylpyridine and divinylbenzene.

15. The method of claim 9 where the impregnant is selected from ultraviolet absorbing substances, steroids, insect repellants, retinoids, fragrances, minoxidil, and emollients.

16. The method of claim 15 where the impregnant is an ultraviolet absorbing substance.

17. The composition of claim 7 where the impregnant is minoxidil.

18. The method of claim 15 where the impregnant is minoxidil.

* * * * *